(12) United States Patent
Hiley

(10) Patent No.: US 10,171,066 B2
(45) Date of Patent: Jan. 1, 2019

(54) COMPACT HIGH VOLTAGE RF GENERATOR USING A SELF-RESONANT INDUCTOR

(71) Applicant: Smiths Detection-Watford Limited, Watford (GB)

(72) Inventor: Alex Paul Hiley, Woking (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 141 days.

(21) Appl. No.: 15/262,148

(22) Filed: Sep. 12, 2016

(65) Prior Publication Data

US 2016/0380621 A1 Dec. 29, 2016

Related U.S. Application Data

(63) Continuation of application No. 14/400,407, filed as application No. PCT/GB2013/051253 on May 15, 2013, now Pat. No. 9,463,468.

(60) Provisional application No. 61/647,143, filed on May 15, 2012.

(51) Int. Cl.
| | |
|---|---|
| *H03K 3/012* | (2006.01) |
| *H03H 7/38* | (2006.01) |
| *B03B 5/08* | (2006.01) |
| *G01N 27/62* | (2006.01) |
| *H01F 19/04* | (2006.01) |
| *H01F 27/255* | (2006.01) |
| *H01F 27/28* | (2006.01) |

(52) U.S. Cl.
CPC .............. *H03K 3/012* (2013.01); *B03B 5/08* (2013.01); *G01N 27/622* (2013.01); *H01F 19/04* (2013.01); *H01F 27/255* (2013.01); *H01F 27/28* (2013.01); *H03H 7/38* (2013.01)

(58) Field of Classification Search
CPC ...................................... H03K 3/012
USPC ......................................... 327/111
See application file for complete search history.

(56) References Cited

U.S. PATENT DOCUMENTS

| | | | |
|---|---|---|---|
| 3,670,406 A | * | 6/1972 | Weber ............... H01F 27/24 29/593 |
| 4,267,404 A | | 5/1981 | Rohde |
| 4,342,013 A | | 7/1982 | Kallman |
| 5,801,379 A | | 9/1998 | Kouznetsov |
| 6,107,628 A | | 8/2000 | Smith et al. |
| 7,161,142 B1 | | 1/2007 | Patterson et al. |
| 7,579,589 B2 | | 8/2009 | Miller et al. |

(Continued)

FOREIGN PATENT DOCUMENTS

| | | |
|---|---|---|
| CN | 101754568 A | 6/2010 |
| CN | 102324374 A | 1/2012 |

(Continued)

OTHER PUBLICATIONS

Office Action dated Jun. 7, 2016 for Chinese Appln. No. 201380037647.5.

(Continued)

*Primary Examiner* — Joseph Chang
(74) *Attorney, Agent, or Firm* — Kevin E. West; Advent, LLP

(57) ABSTRACT

RF generators including active devices driving series resonant circuits are described. The series resonant circuits include a self-resonant dual inductor. The RF generators can be used to drive capacitive loads.

12 Claims, 5 Drawing Sheets

(56) References Cited

U.S. PATENT DOCUMENTS

| | | |
|---|---|---|
| 2005/0269500 A1 | 12/2005 | Potvin et al. |
| 2007/0176704 A1 | 8/2007 | Gabara |
| 2011/0163729 A1 | 7/2011 | Issa et al. |

FOREIGN PATENT DOCUMENTS

| | | |
|---|---|---|
| JP | 2005512274 A | 4/2005 |
| JP | 2007235580 A | 9/2007 |
| JP | 2008153254 A | 7/2008 |
| JP | 2011199385 A | 10/2011 |
| RU | 2008110607 A | 9/2009 |

OTHER PUBLICATIONS

Office Action dated Feb. 16, 2016 for Mexican Appln. No. 11347.
Office Action dated Aug. 17, 2016 for Mexican Appln. No. 64836.
Office Action and Search Report dated May 11, 2017 for RU Appln. No. 2014147136/28(075874).
Office Action dated Aug. 8, 2017 for Japanese Appln. No. 2015-512126.

\* cited by examiner

US 10,171,066 B2

COMPACT HIGH VOLTAGE RF GENERATOR USING A SELF-RESONANT INDUCTOR

BACKGROUND OF THE INVENTION

Field of the Invention

The present invention relates generally to radio frequency (RF) generators and more particularly to RF generator circuits using an inductor.

RF generators produce high frequency signals useful for many applications, for example, for use in ion mobility spectrometers (IMS) and field asymmetric ion mobility spectrometers (FAIMS) or differential mobility spectrometers (DMS). In a spectrometer, molecules in a sample of air are ionized and are admitted into a drive region of a cell. The ionized molecules drift to the opposite end of the cell at a speed dependent on the size of the ion to a collector, which causes a current pulse in the collector. The current into the collector is converted to a voltage and amplified. By measuring the time of flight along the cell it is possible to identify the ion.

The subject matter discussed in this background of the invention section should not be assumed to be prior art merely as result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

SUMMARY OF THE INVENTION

RF generator circuits including a series resonant circuit are described. In one embodiment, an RF generator circuit includes an active device driving the series resonant circuit that includes a bifilar toroidal dual inductor. The RF generator circuits may be used to produce: a high load voltage at a high frequency to drive a capacitive load.

In one aspect, an embodiment of a circuit including a dual inductor is provided. The dual inductor includes a toroidal core. The circuit includes a winding on the toroidal core. The winding includes an input and an output. The circuit also includes another winding on the toroidal core. The another winding includes an input and an output. The circuit also includes a capacitor electrically coupled to the input of the one winding in parallel with the one winding. The circuit also includes another capacitor electrically coupled to the input of the another winding in parallel with the another winding. The outputs of the windings are configured to electrically couple to a capacitive load.

In another aspect, an embodiment of an RF generator circuit including a power supply, an active device configured to output a signal, a dual inductor including a pair of windings wound on a toroidal core, and a capacitor is provided. The capacitor is electrically coupled with one of the windings of the dual inductor. The power supply and the active device are electrically coupled with the capacitor and the one of the windings of the dual inductor. The dual inductor is configured to provide a voltage step up of the signal of the active device.

Another embodiment of the invention relates to a method of generating a signal. The method includes providing a drive signal to an active device. The method also includes providing a power supply. The method also includes providing a circuit a bifilar toroidal dual inductor and capacitor electrically coupled in parallel with at least one of the windings of the bifilar toroidal dual inductor. The active device and the power supply are electrically coupled to the circuit. The method also includes driving a capacitive load electrically coupled to the circuit in series with the bifilar toroidal dual inductor.

This Summary of the Invention is provided to introduce a selection of concepts in a simplified form that are further described below in the Detailed Description. This Summary of the Invention is not intended to identify key features or essential features of the claimed subject matter, nor is it intended to be used to limit the scope of the claimed subject matter.

DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

DETAILED DESCRIPTION OF AN EXEMPLARY EMBODIMENT

Prior to turning to the figures, in one embodiment, an RF generator using an active device to drive a series resonant circuit including a self-resonant dual inductor is provided. In one embodiment, the RF generator produces two antiphase outputs at a higher voltage than a supply voltage of the RF generator at a frequency of at least one Megahertz (MHz). Such outputs may be used to drive a capacitive load. An embodiment of a self-resonant dual inductor is first described.

Figure 1:
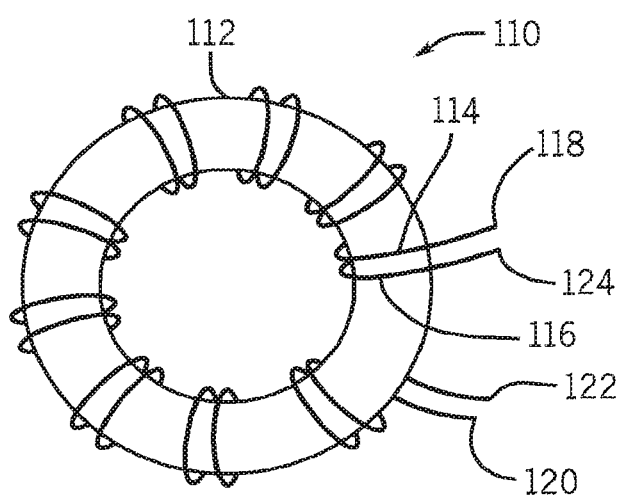
FIG. 1 is a schematic illustration of a self-resonant dual inductor in accordance with an embodiment of this disclosure.

A self-resonant dual inductor, illustrated as a bifilar toroidal dual inductor 110 in FIG. 1 is provided. The bifilar toroidal dual inductor 110 includes a generally toroid-shaped core 112. In one embodiment, the core 112 is a low permeability magnetic core (e.g., formed from iron powder, ferrite, or other suitable materials). Particularly, for example, in one embodiment the core 112 is formed from T 80-6 iron powder.

The core 112 is wrapped with a pair of windings 114 and 116. The windings 114 and 116 are insulated conductors. In one embodiment the material insulating the conductors has low RF loss and high breakdown voltage characteristics, such as, for example, polytetrafluoroethylene (PTFE), or other suitable materials. The windings 114 and 116 are coupled. The winding 114 provides an input 118 and an output 120. Likewise, the winding 116 provides an input 122 and an output 124. Embodiments of a bifilar toroidal dual inductor 110 provide a low radiated magnetic field and, in some embodiments, a smaller size than an air-gap inductor. Additionally, in some embodiments, the bifilar winding configuration provides close coupling between windings and simple construction. In one embodiment, the core 112 is not a split core (i.e., does not have an air gap).

Figure 2:
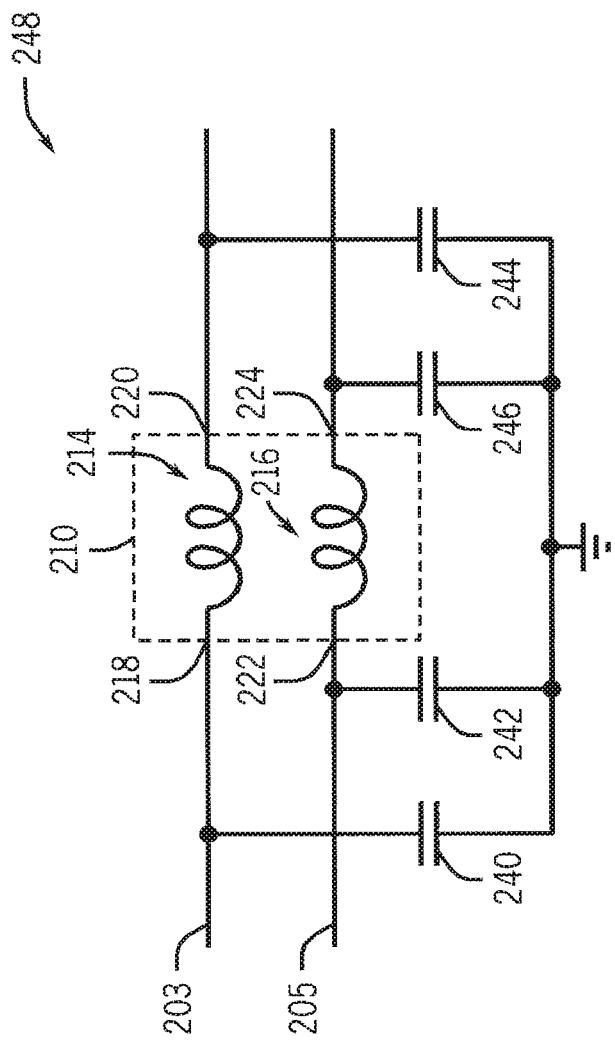
FIG. 2 is a schematic illustration of a self-resonant dual inductor in a series resonant circuit in accordance with an embodiment of this disclosure.

Such a bifilar toroidal dual inductor 110 may be used in various circuits. FIG. 2 illustrates a series resonant circuit 248 including a self-resonant dual inductor, such as the bifilar toroidal dual inductor 210. One input 203 to the circuit 248 is electrically coupled with a capacitor 240 and the input 23 of the winding 214 of the bifilar toroidal dual inductor 210. The capacitor 240 is also electrically coupled to ground. Another input 205 to the circuit 248 is electrically coupled with another capacitor 242 and the input 222 of the winding 216 of the bifilar toroidal dual inductor 210. The capacitor 242 is also electrically coupled to ground. The output 220 of the winding 214 is electrically coupled to a capacitor 244. The capacitor 244 is also electrically coupled to ground. The output 224 of the winding 216 is electrically coupled to a capacitor 246. The capacitor 246 is also electrically coupled to ground.

Two inputs, with phases shifted from one another, may be applied to the inputs 203 and 205 of the series resonant circuit 248. The inductors of the bifilar toroidal dual inductor 210 are coupled, and the bifilar toroidal dual inductor 210 is a self-resonant dual inductor that produces two antiphase outputs. As illustrated in FIGS. 1 and 2, the bifilar toroidal inductor 310 is configured such that current flow through the windings 214 and 216 is in opposite directions. The inter-winding capacitance of the bifilar toroidal dual inductor 210 provides series resonance.

Figure 3:
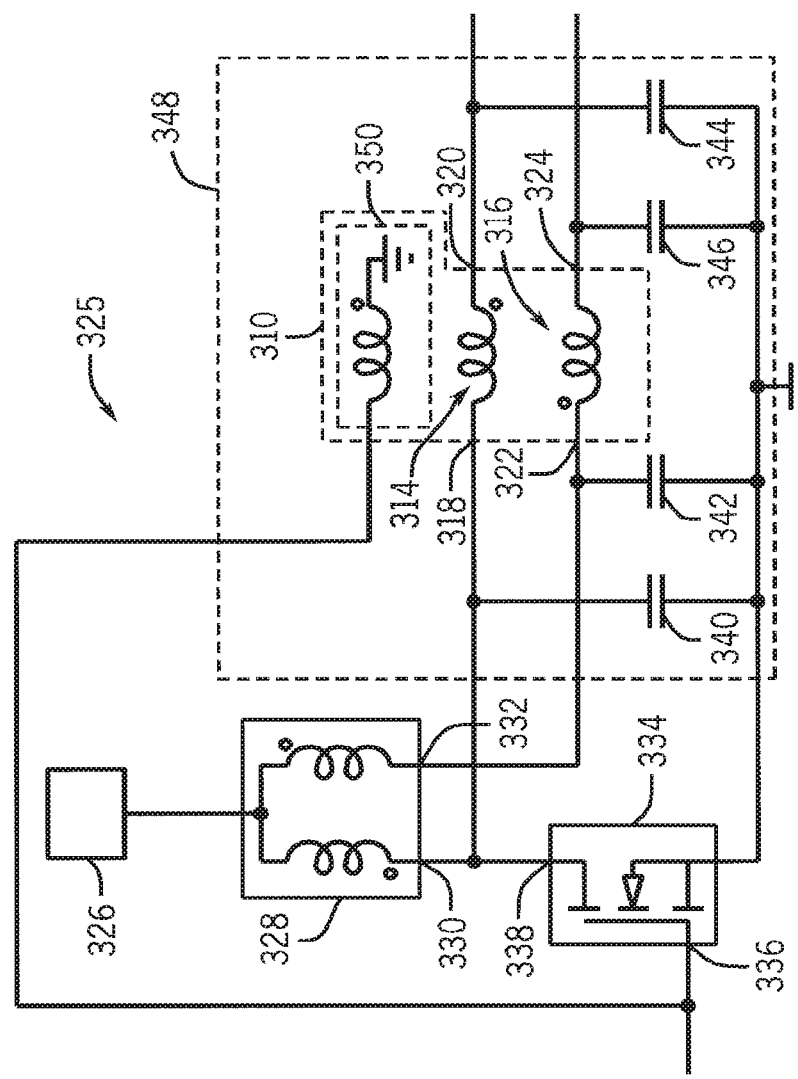
FIG. 3 is a schematic illustration of an embodiment of an RF generator circuit including an embodiment of a series resonant circuit with a self-resonant dual inductor in accordance with an embodiment of this disclosure.

FIG. 3 is a schematic illustration of an embodiment an RF generator circuit 325 including a self-resonant dual inductor, illustrated as a bifilar toroidal dual inductor 310. A power supply, illustrated as a low voltage DO power supply 326 in FIG. 3, is provided. The DO power supply 326 is electrically coupled with a transformer 328. The transformer 328 has two outputs 330 and 332. The transformer 328 produces two outputs that are out of phase with one another at the outputs 330 and 332.

An active device, illustrated as a transistor 334, is also provided. While the transistor 334 is illustrated as an NMOS field effect transistor in FIG. 3, in other embodiments other suitable transistors (e.g., PMOS FET's, JFET's, BJT's, etc.) are used. Additionally, any other suitable active device may be used. The transistor 334 receives a drive signal at an input 336. The source of the transistor 334 is electrically coupled to ground.

The output 338 of the transistor 334, in the illustrated embodiment the drain of the transistor 334, and the first output 330 of the transformer 328 are electrically coupled with the input 318 of the winding 314 of the bifilar toroidal dual inductor 310 and to the first capacitor 340. The first capacitor 340 is electrically coupled in parallel with the winding 314 and is also electrically coupled to ground.

The second output 332 of the transformer 328 is electrically coupled with the second capacitor 342 and the input 322 of the winding 316 of the bifilar toroidal inductor 310. The second capacitor 342 is electrically coupled in parallel with the winding 316 and is also electrically coupled to ground.

The inductors of the bifilar toroidal dual inductor 310 are closely coupled. The bifilar toroidal dual inductor 310 is a self-resonant dual inductor that produces two antiphase outputs. As illustrated in FIG. 3, the bifilar toroidal inductor 310 is configured such that current flow through the windings 314 and 316 is in opposite directions. The outputs 320 and 324 may be used to drive a capacitive load, illustrated in FIG. 3 (along with any stray capacitance in the dual inductor) as capacitors 344 and 346.

The circuit of FIG. 3 is driven such that the bifilar toroidal dual inductor 310 resonates with a load capacitance, illustrated in FIG. 3 (along with any stray capacitance in the dual inductor) as capacitors 344 and 346. The series resonant circuit 348 is driven at its resonant frequency to provide a voltage step up, such that outputs 320 and 324 will be at a higher voltage than the inputs 318 and 322. With a high frequency signal and the bifilar toroidal inductor 310 resonating with the lead capacitance 344 and 346, low power may be used to produce the higher voltage at the high frequency at the high voltage outputs 320 and 324. Thus, an impedance matching series resonant circuit 348 is provided for low power, high frequency voltage step up. The bifilar toroidal dual inductor 310 is configured such that the inter-winding capacitance provides a series resonance and a large voltage step-up.

In one embodiment, a bifilar toroidal dual inductor with a T 80-6 iron power core is provided. The core has a 20 millimeter outside diameter and is 6 millimeters thick. The core is would with two windings, each with 35 turns. When the core is driven at 8 MHz with a supply voltage of 30 V, a differential output of 3 kV peak-to-peak is achieved.

Voltage step up is dependent on the quality factor ("Q") of the impedance matching series resonant circuit 348. Both the quality factor and the resonant frequency of the series resonant circuit 348 may vary based on multiple different factors (e.g., temperature, component design, etc.). Feedback, e.g., through use of, for example, a feedback device, allows for regulation and stabilization of the output voltage of the network 348.

In one embodiment, a feedback device, illustrated as a small feedback winding 350 (e.g., 1 turn) wound to the bifilar toroidal dual inductor 310, is provided. The feedback winding 350 is electrically coupled with the input 336 of the active device 334. Thus, the RF generator circuit 325 will be self-oscillating, with the active device continuing to drive the series resonant circuit 348 at its resonant frequency. This provides for an efficient RF generator circuit 325.

Figure 4:
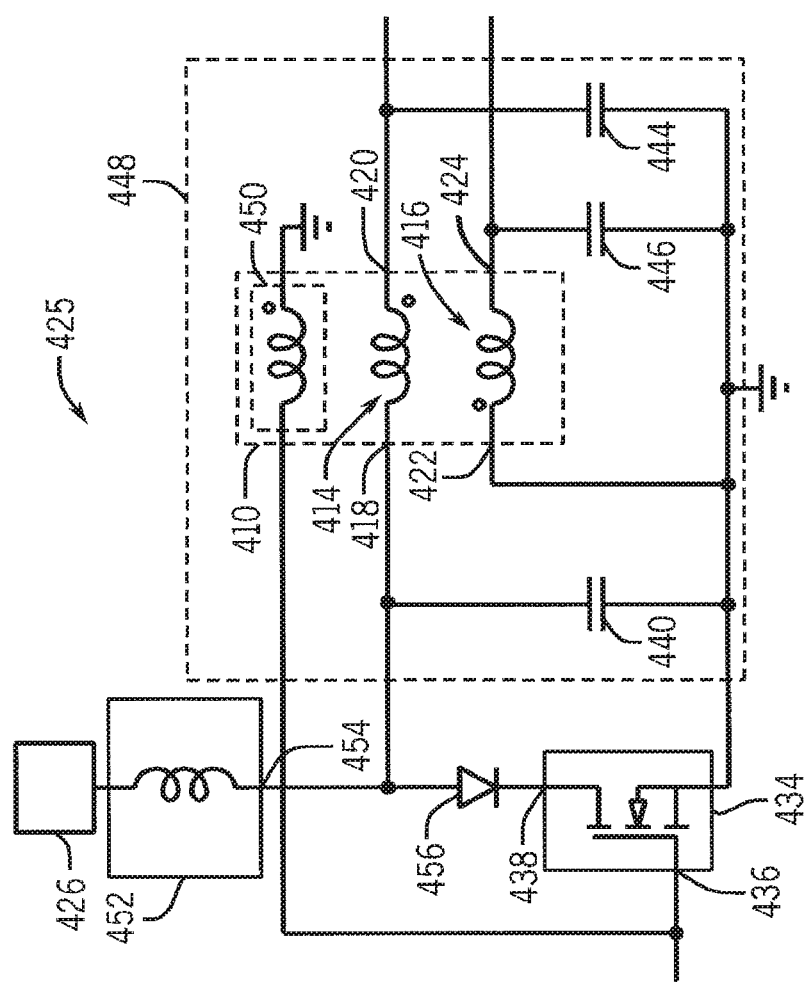
FIG. 4 is a schematic illustration of another embodiment of an RF generator circuit including an embodiment of a series resonant circuit with a self-resonant dual inductor in accordance with an embodiment of this disclosure.

FIG. 4 is a schematic illustration of another embodiment of an RF generator circuit 425 including a self-resonant dual inductor illustrated as a bifilar toroidal dual inductor 410. A power supply, illustrated as a low voltage DC power supply 426 an FIG. 4, is provided. The DC power supply 426 is electrically fed through an inductor 452 with an output 454.

An active device, illustrated as a transistor 434 an FIG. 4, is also provided. The transistor 434 receives a drive signal at its input 486. The source of the transistor 484 is electrically coupled to ground. The output 438 of the transistor 434, in the illustrated embodiment the drain of the NMOS field effect transistor, is electrically coupled in series with a diode 456.

The diode 456 and the output 454 of the inductor 452 are electrically coupled to the input 418 of the winding 414 of the bifilar toroidal dual inductor 410 and to a first capacitor 440. The first capacitor 440 is electrically coupled in parallel with the winding 414 and is also electrically coupled to ground. The input 422 of the winding of the bifilar toroidal dual inductor 410 is electrically coupled to ground.

The outputs 420 and 424 are configured to be coupled in series with and drive a capacitive load. The capacitive load (along with stray capacitance of the bifilar toroidal dual inductor 410) is schematically represented as load capacitors 444 and 446, which are coupled to the output 420 and the output 424 respectively.

The circuit of FIG. 4 is driven such that the bifilar toroidal dual inductor 410 resonates with the load capacitance 444 and 446 (along with any stray capacitance in the bifilar toroidal dual inductor 410). With a high frequency signal and the bifilar toroidal inductor 410 resonating with the load capacitance 444 and 446, low supply power is used to produce the higher voltage at the high frequency at the outputs 420 and 424 of the bifilar toroidal dual inductor 410. Thus, an impedance matching series resonant circuit 448 provides low power, high frequency voltage step up. The bifilar toroidal inductor 410 is configured such that the interwinding capacitance provides a series resonance and a large voltage step-up.

In one embodiment, a feedback device, illustrated as a small feedback winding 450 (e.g., 1 turn) would to the bifilar toroidal dual inductor 410, is provided. The feedback winding 450 is electrically coupled with the active device 434. Thus, the RF generator circuit 425 will be self-oscillating and may be driven at the resonant frequency. This provides for an efficient RF generator circuit 425.

In one embodiment, the diode 456 prevents the parasitic body diode of the NMOS field effect transistor from clamping and limiting the initial voltage swing which drives the series resonant circuit 448 including the bifilar toroidal dual inductor 410. Additionally, the diode 456 allows the voltage applied to the series resonant circuit 448 to swing negative, giving the series resonant circuit 448 a greater output.

Figure 5:
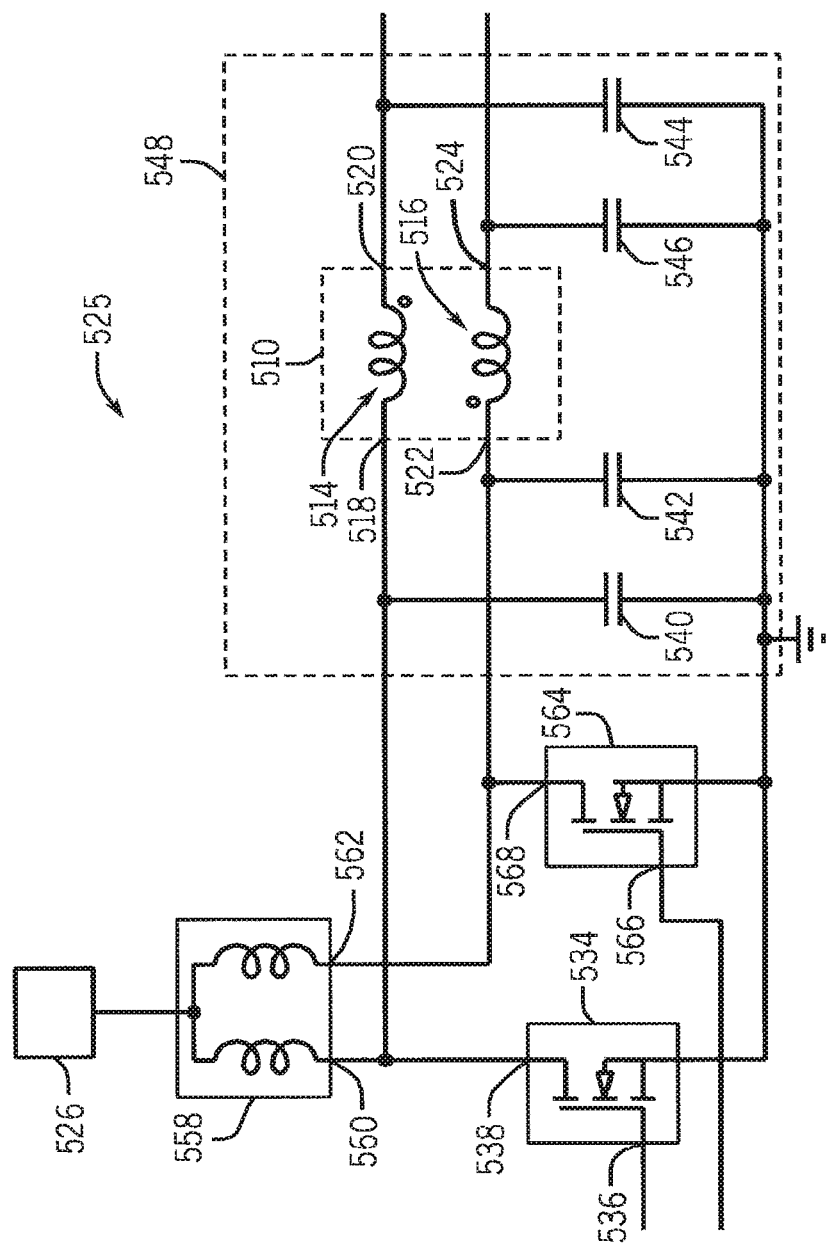
FIG. 5 is a schematic illustration of another embodiment of an RF generator circuit including an embodiment of a series resonant circuit with a self-resonant dual inductor in accordance with an embodiment of this disclosure.

FIG. 5 illustrates another embodiment of an RF generator circuit 525 including a self-resonant dual inductor illustrated as a bifilar toroidal dual inductor 510. A power supply, illustrated as a low voltage DC power supply 526 in FIG. 5, is provided. The DC power supply 526 is electrically coupled to a transformer 558. The transformer 558 includes two outputs 560 and 562.

Two active devices, illustrated as transistors 534 and 564 in FIG. 5, are also provided. The transistor 534 receives a drive signal at its input 536. The source of the transistor 534 is electrically coupled to ground. The output 538 of the transistor 534 and the output 560 of the transformer 560 are electrically coupled to a first capacitor 540 and to the input 518 of the winding 514 of the bifilar toroidal dual inductor 510. The first capacitor 540 is electrically coupled in parallel with the winding 514 and is also electrically coupled to ground.

The transistor 564 also receives a drive signal at its input 566. The source of the transistor 564 is electrically coupled to ground. The output 568 of the transistor 564 and the output 562 of the transformer 558 are electrically coupled to a second capacitor 542 and to the input 522 of the winding 516 of the bifilar toroidal dual inductor 510. The second capacitor 542 is electrically coupled in parallel with the winding 516 and is also electrically coupled to ground.

The outputs 520 and 524 of the windings 514 and 516 are configured to be coupled in series with and drive a capacitive load. The capacitive load (along with stray capacitance of the bifilar toroidal dual inductor 510) is schematically represented as load capacitors 544 and 546, which are coupled to the output 420 and the output 424 respectively.

The circuit of FIG. 5 is driven such that the bifilar toroidal dual inductor 510 resonates with the load capacitance 544 and 546 (along with any stray capacitance in the bifilar toroidal dual inductor 510). With a high frequency signal and the bifilar toroidal inductor 510 resonating with the load capacitance 544 and 546, low supply power is used to produce the higher voltage at the high frequency at the outputs 520 and 524 of the bifilar toroidal dual inductor 510. Thus, an impedance matching series resonant circuit 548 provides low power, high frequency voltage step up. The bifilar toroidal inductor 510 is configured such that the interwinding capacitance provides a series resonance and a large voltage step-up.

Some applications may require a high frequency, high voltage, waveform, such as those produced by embodiments of RF generator circuits as described above. For example, on modifiers, such as those described in U.S. Patent Application Publication No. 2011/0300638, assigned to the assignee of the present application and incorporated herein by reference in its entirety, may utilize a high frequency waveform. Embodiments of RF generator circuits as described herein may be used to supply high frequency waveforms to such ion modifiers. Additionally, embodiments of RF generator circuits producing high frequency waveforms may be utilized in various other applications.

Embodiments of RF generators including series resonant circuits including a bifilar toroidal dual inductor as disclosed herein may provide high output voltage at high frequency (e.g., at least several MHz). A bifilar toroidal dual inductor may provide a desired resonant frequency, while having a small size and a low radiated magnetic field. Additionally, the stray capacitance between the windings of a bifilar toroidal dual inductor may provide self-resonance. Additionally, in one embodiment a bifilar toroidal dual inductor does not require an air gap, provides close coupling, and is of simple construction. A toroidal core may comprise any ring shape which need not be circular, for example it may be square, ellipsoid, rectangular, or any other closed shape. In one embodiment a toroidal core comprises a torpid shape.

While the active devices in each of the embodiments are illustrated as NMOS field effect transistors, in other embodiments other suitable transistors (e.g., PMOS FET's, JFET's, BJT's, etc.) are used. Additionally, any other suitable active device, such as a voltage controlled impedance, may be used.

The feedback device and the diode disclosed with regard to the above embodiments, may be used in conjunction with any of the embodiments disclosed herein.

While the self-resonant dual inductor is illustrated as a bifilar toroidal dual inductor, in other embodiments, other suitable types of self-resonant dual inductors are used.

In an embodiment there is provided an RF circuit for providing a radio frequency signal, the circuit comprising: a dual inductor including one winding including an input and an output, and another winding including an input and an output; wherein the one winding and the another winding are arranged to provide, between the one winding and the another winding, a parasitic capacitance selected to determine the frequency of the radio frequency signal; and wherein the outputs of the windings are configured to electrically couple to a capacitive load. The one winding and the another winding can be spatially arranged so the selected parasitic capacitance and the inductance of the dual inductor provide a resonant circuit having an RF resonant frequency. For example the resonant frequency provided by the inductance of the dual inductor and the selected parasitic capacitance may be at least 0.5 MHz, or at least 1 MHz, or at least 3 MHz. In some of these possibilities the resonant frequency provided by the inductance of the dual inductor and the selected parasitic capacitance may be less than 15 MHz, or less than 50 MHz. The spatial arrangement of the windings may comprise selecting the length of the windings, and the spacing between them and/or the dielectric constant of any coating on the winding. In an embodiment the RF circuit further comprises the capacitive load, and the selected parasitic capacitance, and the capacitive load, and the inductance of the dual inductor cooperate to provide a resonant circuit having an RF resonant frequency. The capacitive load may comprise an ion modifier of an ion mobility spectrometer.

The dual inductor may comprise a ferrite or iron powder core onto which the windings are wound. The core may be arranged in a closed, loop shape, such as a toroid. In some embodiments, no core, or a non-magnetic core may be used.

The drawings show capacitors 244, 246, in FIG. 2, 344, 346, in FIG. 3, and 444, 446 in FIG. 4. These capacitors are a representation of the distributed capacitance between the windings of the dual inductor and any capacitance of a load coupled between the output of the windings. They are not intended to indicate actual capacitors. It will therefore be appreciated that the representation in the drawings is merely schematic, and most of the capacitance is actually between the outputs of the winding, rather than between each output and ground. In some possibilities capacitors may be added at the positions indicated by 244, 246, in FIG. 2, 344, 346, in FIG. 3, and 444, 446 in FIG. 4 in order to tune the circuit.

In an embodiment there is provided an ion modification circuit for an ion mobility spectrometer comprising: an ion modifier for subjecting ions in a drift tube of an ion mobility spectrometer to a radio frequency electric field; and a dual inductor including one winding including an input and an output, and another winding including an input and an output; wherein the one winding and the another winding are arranged to provide, between the one winding and the another winding, a parasitic capacitance, and the outputs of the windings are coupled to the ion modifier, wherein the parasitic capacitance of the dual inductor is selected based on the inductance of the dual inductor and the capacitance of the ion modifier to provide a resonant circuit having an RF resonant frequency. In an embodiment the resonant frequency is at least 3 MHz, and in some examples of this embodiment the resonant frequency is less than 15 MHz. This resonant circuit may comprise the features of any of the circuits described herein.

The ion modifier may comprise a first electrode, and a second electrode, wherein the electrodes are configured to be arranged across the drift tube for subjecting ions in the drift tube to a radio frequency electric field between the electrodes.

In an embodiment the one winding and the another winding are arranged so that an alternating current in the one winding induces an alternating current having opposing phase in the another winding.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., such as) provided herein, is intended merely to better illuminate the invention and does not pose a limitation on the scope of the invention unless otherwise claimed. No language in the specification should be construed as indicating any non-claimed element as essential to the practice of the invention.

While reference is made to amplifiers and amplification elements, it is not intended that an amplifier or an amplification element be limited to a single element. Instead, it is envisioned that these terms may in some embodiments encompass circuits including multiple elements, integrated circuits, or any other arrangement suitable for amplification. The terms "stray capacitance" and "parasitic capacitance" are used interchangeably herein to refer to an inherent capacitance associated with arranging charge carrying conductors in proximity to one another.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

What is claimed is:

1. An RF circuit for providing a radio frequency signal, the circuit comprising:
    a dual inductor including one winding including an input and an output, and another winding including an input and an output;
    wherein the one winding and the another winding are arranged to provide, between the one winding and the another winding, a parasitic capacitance selected to determine the frequency of the radio frequency signal; and
    wherein the outputs of the windings are configured to electrically couple to a capacitive load.

2. The RF circuit of claim 1 in which the one winding and the another winding are spatially arranged so the selected parasitic capacitance and the inductance of the dual inductor provide a resonant circuit having an RF resonant frequency.

3. The RF circuit of claim 2 further comprising the capacitive load, and in which the selected parasitic capacitance, and the capacitive load, and the inductance of the dual inductor provide a resonant circuit having an RF resonant frequency.

4. The RF circuit of claim 1 in which the dual inductor comprises a ferrite or iron powder core.

5. The RF circuit of claim 4 in which the core is a closed loop shape, and the one winding and the another winding are wound onto the core.

6. The RF circuit of claim 1 in which the one winding and the another winding are arranged so that an alternating current in the one winding induces an alternating current having opposing phase in the another winding.

7. The RF circuit of claim 2 in which the dual inductor comprises a ferrite or iron powder core.

8. The RF circuit of claim 3 in which the dual inductor comprises a ferrite or iron powder core.

9. The RF circuit of claim 2 in which the one winding and the another winding are arranged so that an alternating current in the one winding induces an alternating current having opposing phase in the another winding.

10. The RF circuit of claim 3 in which the one winding and the another winding are arranged so that an alternating current in the one winding induces an alternating current having opposing phase in the another winding.

11. The RF circuit of claim 4 in which the one winding and the another winding are arranged so that an alternating current in the one winding induces an alternating current having opposing phase in the another winding.

12. The RF circuit of claim 5 in which the one winding and the another winding are arranged so that an alternating current in the one winding induces an alternating current having opposing phase in the another winding.

* * * * *